United States Patent
Forsell

(10) Patent No.: US 6,463,935 B1
(45) Date of Patent: *Oct. 15, 2002

(54) CONTROLLED HEARTBURN AND REFLUX DISEASE TREATMENT

(75) Inventor: Peter Forsell, Menzingen (CH)

(73) Assignee: Obtech Medical AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/501,571

(22) Filed: Feb. 10, 2000

(51) Int. Cl.[7] .................................................. A61F 2/02
(52) U.S. Cl. ........................................... 128/899; 600/37
(58) Field of Search ................................. 128/897–899; 600/29–32, 37, 593; 604/27–28; 606/139–141, 151, 157, 201–203, 213, 228; 607/41

(56) References Cited

U.S. PATENT DOCUMENTS

| | | | | |
|---|---|---|---|---|
| 3,750,194 A | * | 8/1973 | Summers | 600/31 X |
| 3,875,928 A | * | 4/1975 | Angelchik | 600/37 |
| 4,246,893 A | * | 1/1981 | Berson | 128/898 |
| 4,271,827 A | | 6/1981 | Angelchik | |
| 4,592,355 A | * | 6/1986 | Antebi | 606/144 |
| 4,696,288 A | * | 9/1987 | Kuzmak et al. | 128/898 |
| 5,006,106 A | * | 4/1991 | Angelchik | 128/898 |
| 5,042,084 A | | 8/1991 | Daly | |
| 5,074,868 A | * | 12/1991 | Kuzmak | 606/157 |
| 5,160,338 A | * | 11/1992 | Vincent | 606/157 |
| 5,226,429 A | * | 7/1993 | Kuzmak | 128/898 |
| 5,316,543 A | * | 5/1994 | Eberbach | 128/897 |
| 5,449,368 A | * | 9/1995 | Kuzmak | 606/157 |
| 5,509,888 A | * | 4/1996 | Miller | 600/29 |
| 5,704,893 A | * | 1/1998 | Timm | 600/29 |
| 5,769,877 A | * | 6/1998 | Barreras | 607/61 |
| 5,910,149 A | * | 6/1999 | Kuzmak | 606/157 |
| 5,938,669 A | * | 8/1999 | Klaiber et al. | 606/157 |
| 5,978,712 A | * | 11/1999 | Suda et al. | 607/41 |
| 6,074,341 A | * | 6/2000 | Anderson et al. | 600/29 |

FOREIGN PATENT DOCUMENTS

| | | |
|---|---|---|
| WO | WO 00/09048 | 2/2000 |
| WO | WO 00/15158 | 3/2000 |
| WO | WO 01/12078 | 2/2001 |

* cited by examiner

Primary Examiner—Kevin Shaver
Assistant Examiner—Joseph A. Cadugan
(74) Attorney, Agent, or Firm—Nixon & Vanderhye, P.C.

(57) ABSTRACT

A heartburn and reflux disease treatment apparatus and method include and utilize: an operable restriction device implanted in a patient and engaging the stomach close to the cardia or engaging the esophagus to form a restricted passageway in the stomach or esophagus, a source of energy for energizing the restriction device, and a control device for releasing energy from the source of energy from outside the patient's body. The released energy is used in connection with the operation of the restriction device including to enlarge or contract the restricted passageway.

127 Claims, 6 Drawing Sheets

CONTROLLED HEARTBURN AND REFLUX DISEASE TREATMENT

CROSS REFERENCE TO RELATED APPLICATION

This application incorporates herein by reference the disclosure of provisional application serial No. 60/148,345 filed Aug. 12, 1999.

BACKGROUND OF THE INVENTION

The present invention relates to a heartburn and reflux disease treatment apparatus and method. More specifically, the invention relates to a heartburn and reflux disease treatment apparatus and method for surgical application in the abdomen of a patient for forming a restricted food passageway in the esophagus or stomach. The term "patient" includes an animal or a human being.

Heartburn and reflux disease is a widespread medical problem. This is often due to hiatal hernia, i.e. a portion of the stomach immediately below the gastric fundus slides upwardly through the esophageal hiatus. In consequence, stomach acids and foods are regurgitated into the esophagus.

In the late 1970s a prior art prosthesis called Angelchik, according to U.S. Pat. No. 3,875,928, was used to operatively treat heartburn and reflux disease. However, the Angelchik prosthesis had a major disadvantage in that it was not possible to adjust the size of the restriction opening after the operation. A further disadvantage was that the prosthesis did not satisfactorily protect the esophagus and the surrounding area against injuries due to poor shape of the prosthesis. Therefore, operations using the Angelchik prosthesis are no longer practised.

An operation technique, semi-fundoduplicatio, is currently in use for treating heartburn and reflux disease. A most common operation is Nissen semi-fundoduplicatio, in which one takes the fundus of the stomach and makes a three quarter of a turn around the esophagus and suture between the stomach and esophagus. Although this operation works fairly well it has three main disadvantages. Firstly, most patients treated in accordance to "ad modum Nissen" lose their ability to belch. Secondly, many of these patients get dysphagia, i.e. difficulties to swallow after the operation. Thirdly, it is not possible to adjust the food passageway in the esophagus or stomach in any way after the operation. Characteristic for these patients is the variation of their problems over the day. For example, many patients have difficulties during the night when they lie down because of stomach acid leaking up into the esophagus.

SUMMARY OF THE INVENTION

It is an object of the present invention to provide a new convenient heartburn and reflux disease treatment apparatus, the performance of which may be affected by the patient at any time after operation, in particular when various needs arise over the day, so that the patient always is satisfied.

Accordingly, there is provided a heartburn and reflux disease treatment apparatus, comprising an operable restriction device implanted in a patient and engaging the stomach close to the cardia or engaging the esophagus to form a restricted food passageway in the stomach or esophagus, a source of energy for energizing the restriction device, and a control device operable from outside the patient's body for releasing energy from the source of energy, wherein the released energy is used in connection with the operation of the restriction device.

As a result, the advantage is achieved that the implanted restriction device can be non-invasively operated, when the restriction device has to be adjusted. Furthermore, the apparatus of the invention provides a simple and effective control of the energy supplied to implanted components of the apparatus which ensures long reliable function of the apparatus, possibly for the rest of the patient's life.

The restriction device preferably controls the cross-sectional area of the food passageway in the stomach or esophagus, which gives the advantage that the patient is enabled to adjust the cross-sectional area of the food passageway whenever he likes during the day. This advantage should not be underestimated, because in case the patient would need to vomit it would be very difficult for him to do so if he were unable to immediately enlarge the cross-sectional area of the food passageway.

The control device may also control the restriction device. The control device may comprise an internal control unit, preferably including a microprocessor, implanted in the patient for controlling the restriction device. The control device may further comprise an external control unit outside the patient's body, wherein the internal control unit is programmable by the external control unit, for example for controlling the restriction device over time. Alternatively, the internal control unit may control the restriction device over time in accordance with an activity schedule program, which may be adapted to the patient's needs.

Conveniently, the external control unit may load the internal control unit with data in accordance with a loading mode only authorized for a doctor. For specialized controls of the restriction device, the external control unit may control the internal control unit in accordance with a doctor mode only authorized for the doctor. For simple controls of the restriction device, the external control unit may control the internal control unit in accordance with a patient mode permitted for the patient. Thus, by using the external control unit in accordance with different modes it is possible to have certain functions of the restriction device controlled by the patient and other more advanced functions controlled by the doctor resulting, which enables a flexible post-operation treatment of the patient.

Generally, the apparatus further comprises an operation device implanted in the patient for operating the restriction device, wherein the control device controls the operation device to operate the restriction device. The control device may directly power the operation device with energy released from the source of energy and/or power other implanted energy consuming components of the apparatus. The term "directly" is used to mean, on one hand, that the operation device is powered with released energy while the latter is being released by the control device, on the other hand, that the released energy may be somewhat delayed, in the order of seconds, by for instance an energy stabilizer before powering the operation device. The advantage of directly using energy as it is released is that the apparatus can be of a very simple design and the few components involved makes the apparatus extremely reliable.

The restriction device may be non-inflatable, i.e. with no hydraulic fluid involved for the adjustments of the restriction device. This eliminates problems with fluid leaking from the restriction device.

The operation device may comprise hydraulic means and at least one valve for controlling a fluid flow in the hydraulic means. The control device may suitably comprise a wireless remote control for controlling the valve. The restriction device may comprise hydraulic means and the operation device may comprise a reservoir forming a fluid chamber with a variable volume connected to the hydraulic means. The operation device may distribute fluid from the chamber to the hydraulic means by reduction of the volume of the chamber and withdraw fluid from the hydraulic means to the chamber by expansion of the volume of the chamber.

In accordance with a first main aspect of the invention, the source of energy is external to the patient's body and the control device releases wireless energy from the source of energy. An energy storage device, preferably an electric accumulator, may be implanted in the patient for storing the wireless energy released from the external source of energy. The electric accumulator may comprise at least one capacitor or at least one rechargeable battery, or a combination of at least one capacitor and at least one rechargeable battery. Alternatively, a battery may be implanted in the patient for supplying electric energy to implanted electric energy consuming components of the apparatus, in addition to the supply of wireless energy. Where the control device comprises an implanted control unit the electronic circuit thereof and the restriction device may be directly powered with transformed wireless energy, or energy from either the implanted energy storage device or battery.

In a first particular embodiment in accordance with the first main aspect of the invention, the operation device comprises a motor, preferably an electric motor which may have electrically conductive parts made of plastics. The motor may include a rotary motor, wherein the control device is adapted to control the rotary motor to rotate a desired number of revolutions. Alternatively, the motor may include a linear motor, or a hydraulic or pneumatic fluid motor, wherein the control device is adapted to control the fluid flow through the fluid motor. Motors currently available on the market are getting smaller and smaller. Furthermore, there is a great variety of control methods and miniaturized control equipment available. For example, a number of revolutions of a rotary motor may be analyzed by a Hall-element just a few mm in size.

In a second particular embodiment in accordance with the first main aspect of the invention, the control device is adapted to shift polarity of the released energy to reverse the operation device. The operation device may suitably comprise an electric motor and the released energy may comprise electric energy.

In a third particular embodiment in accordance with the first main aspect of the invention, the restriction device is operable to perform a reversible function and there is a reversing device implanted in the patient for reversing the function performed by the restriction device. Such a reversing function preferably involves enlarging and restricting the food passageway by the restriction device, suitably in a stepless manner. In this connection, the control device suitably controls the reversing device, which may include a switch, to reverse the function performed by the restriction device. The reversing device may comprise hydraulic means including a valve for shifting the flow direction of a fluid in the hydraulic means. Alternatively, the reversing device may comprise a mechanical reversing device, such as a switch or a gear box.

Where the reversing device comprises a switch the control device suitably controls the operation of the switch by shifting polarity of released energy supplied to the switch. The switch may comprise an electric switch and the source of energy may supply electric energy for the operation of the switch. The switch mentioned above may comprise an electronic switch or, where applicable, a mechanical switch.

In accordance with the third particular embodiment, the operation device preferably comprises a motor, wherein the reversing device reverses the motor.

In a fourth particular embodiment in accordance with the first main aspect of the invention, the restriction device comprises hydraulic means, for example including an expansible/contractible cavity for fluid. The operation device preferably comprises a pump for pumping a fluid in the hydraulic means, a motor for driving the pump, a valveless fluid conduit between the pump and the hydraulic means of the restriction device, and a reservoir for fluid, wherein the reservoir forms part of the conduit. All of the hydraulic components involved are preferably devoid of any non-return valve. This is of great advantage, because with valves involved there is always a risk of malfunction due to improperly working valves, especially when long time periods passes between valve operations. The reservoir may form a fluid chamber with a variable volume, and the pump may distribute fluid from the chamber to the hydraulic means of the restriction device by reduction of the volume of the chamber and withdraw fluid from the hydraulic means to the chamber by expansion of the volume of the chamber.

In accordance with a second main aspect of the invention, the source of energy is implanted in the patient. Thus, the control device releases energy from the implanted source of energy from outside the patient's body. This solution is advantageous for embodiments of the apparatus that have a relatively high energy consumption which cannot be satisfied by direct supply of wireless energy.

The source of energy thus implanted may comprise an accumulator, preferably an electric source of energy, such as a battery having a life-time of at least 10 years.

The above first, second, third and fourth particular embodiments described in connection with the first main aspect of the invention are also applicable in accordance with the second main aspect of the invention, i.e. where the source of energy is implanted.

All of the above embodiments may be combined with at least one implanted sensor for sensing at least one physical parameter of the patient, wherein the control device may control the restriction device in response to sensing by the sensor. For example, the sensor may comprise a pressure sensor for directly or indirectly sensing the pressure in the food passageway. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor. The expression "indirectly sensing the pressure in the food passageway" should be understood to encompass the cases where the sensor senses the pressure against the restriction device or human tissue of the patient. Where the control device comprises an internal control unit implanted in the patient, the internal control unit may suitably directly control the restriction device in response to sensing from the sensor. In response to sensing from the sensor, for example pressure, the patient's position or any other important physical parameter, the internal control unit may send information thereon to outside the patient's body. The control unit may also automatically control the restriction device in response to sensing from the sensor. For example, the control unit may control the restriction device to further restrict the food passageway in the stomach in response to the sensor sensing that the patient is lying, or enlarge the food passageway in response to the sensor sensing an abnormally high pressure against the restriction device.

Where the control device comprises an external control unit outside the patient's body, the external control unit may, suitably directly, control the restriction device in response to sensing from the sensor. The external control unit may store information on the physical parameter sensed by the sensor and may be manually operated to control the restriction device based on the stored information. In addition, there may be at least one implanted sender for sending information on the physical parameter sensed by the sensor.

An external data communicator may be provided outside the patient's body and an internal data communicator may be implanted in the patient for communicating with the external communicator. The implanted communicator may feed data related to the patient, or related to the implanted restriction device, back to the external communicator. Alternatively or in combination, the external communicator may feed data to the internal communicator. The implanted communicator may suitably feed data related to at least one physical signal of the patient.

Generally, the apparatus of the invention may comprise a switch implanted in the patient for directly or indirectly switching the energy released from the source of energy. The restriction device may control the cross-sectional area of the food passageway. For example, the restriction device may be operable to open and close the food passageway or may steplessly control the cross-sectional area of the food passageway. A pressure sensor may be provided for directly or indirectly sensing the pressure in the food passageway. The control device may control the restriction device in response to sensing from the pressure sensor.

The apparatus may comprise an implanted energy transfer device, wherein the control device releases electric energy and the energy transfer device transfers the electric energy into kinetic energy for, preferably direct, operation of the restriction device. Suitably, an implanted stabilizer, such as a capacitor or a rechargeable accumulator, or the like, may be provided for stabilizing the electric energy released by said control device. In addition, the control device may release energy for a determined time period or in a determined number of energy pulses. Finally, the restriction device may be non-inflatable.

All of the above embodiments are preferably remote controlled. Thus, the control device advantageously comprises a wireless remote control transmitting at least one wireless control signal for controlling the restriction device. With such a remote control it will be possible to adapt the function of the apparatus to the patient's need in a daily basis, which is beneficial with respect to the treatment of the patient.

The wireless remote control may be capable of obtaining information on the condition of the implanted restriction device and of controlling the restriction device in response to the information. Also, The remote control may be capable of sending information related to the restriction device from inside the patient's body to the outside thereof.

In a particular embodiment of the invention, the wireless remote control comprises at least one external signal transmitter or tranceiver and at least one internal signal receiver or transciever implanted in the patient. In another particular embodiment of the invention, the wireless remote control comprises at least one external signal reciever or transceiver and at least one internal signal transmitter or transceiver implanted in the patient.

The remote control may transmit a carrier signal for carrying the control signal, wherein the carrier signal is frequency, amplitude or frequency and amplitude modulated and is digital, analog or digital and analog. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

In all of the above solutions, the control device advantageously releases energy from the source of energy in a non-invasive, mechanical or non-mechanical manner.

The control device may release magnetic, electromagnetic, kinetic or thermal energy, or non-magnetic, non-thermal, non-electromagnetic or non-kinetic energy.

Another object of the present invention is to provide methods for treating heartburn and reflux disease.

Accordingly, in accordance with a first alternative there is provided a method of treating heartburn and reflux disease, comprising the steps of implanting an operable restriction device in a patient, so that the restriction device engages the stomach close to the cardia or engages the esophagus to form a restricted food passageway in the stomach or esophagus, providing a source of energy for energizing the restriction device, and controlling the source of energy to release energy for use in connection with the operation of the restriction device. The method may further comprise using energy released from the source of energy to operate the restriction device to enlarge and reduce, respectively, the food pasageway.

In accordance with a second alternative there is provided a method of treating heartburn and reflux disease, comprising the steps of placing at least two laparascopical trocars in a patient's body, inserting a dissecting tool through the trocars and dissecting an area of the stomach or esophagus, placing an operable restriction device in the dissected area, so that the restriction device engages the stomach close to the cardia or engages the esophagus to form a restricted food passageway in the stomach or esophagus, implanting a source of energy in the patient, and controlling the implanted source of energy from outside the patients body to release energy for use in connection with the operation of the restriction device.

In accordance with a third alternative there is provided a method of treating heartburn and reflux disease, comprising the steps of placing at least two laparascopical trocars in a patient's body, inserting a dissecting tool through the trocars and dissecting an area of the stomach or esophagus, implanting an operable restriction device in the dissected area, so that the restriction device engages the stomach close to the cardia or engages the esophagus to form a restricted food passageway in the stomach or esophagus, implanting an energy transfer device in the patient, providing an external source of energy, controlling the external source of energy to release wireless energy, and transferring the wireless energy by the energy transfer device into energy for use in connection with the operation of the restriction device.

DETAILED DESCRIPTION OF THE DRAWINGS

Figure 1:
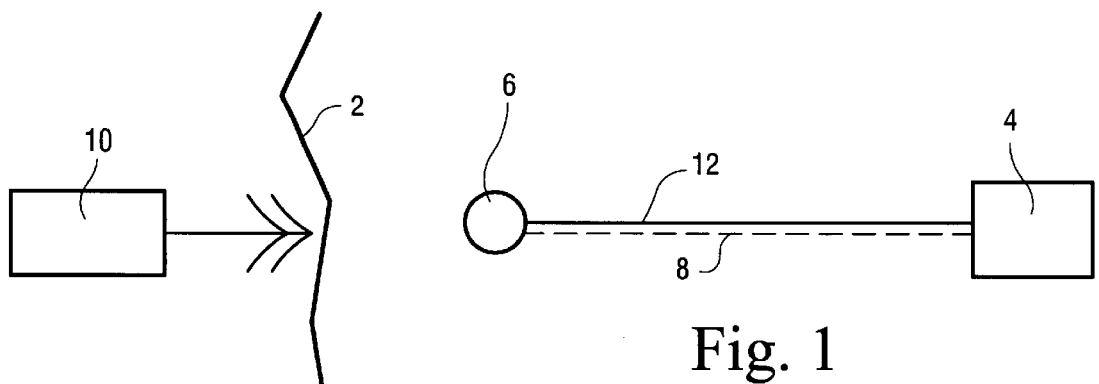
FIGS. 1 to 4 are schematic block diagrams illustrating four embodiments, respectively, of the invention, in which wireless energy is released from an external source of energy.

FIG. 1 schematically shows an embodiment of the heartburn and reflux disease apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body. The apparatus of FIG. 1 comprises an implanted operable restriction device 4, which engages the patient's stomach close to the cardia (or alternatively engages the esophagus) to form a restricted food passageway in the stomach. The restriction device 4 is capable of performing a reversible function, i.e. to enlarge and reduce the cross-sectional area of the food passageway, whereby the restriction device works as an artificial sphincter. An implanted control unit 6 controls the restriction device 4 via a control line 8 to form an adequate size of the cross-section area of the restricted food passageway. An external control unit 10 includes an external source of energy and a wireless remote control transmitting a control signal generated by the external source of energy. The control signal is received by a signal receiver incorporated in the implanted control unit 6, whereby the control unit 6 controls the implanted restriction device 4 in response to the control signal. The implanted control unit 6 also uses energy from the control signal for operating the restriction device 4 via a power supply line 12.

Figure 2:
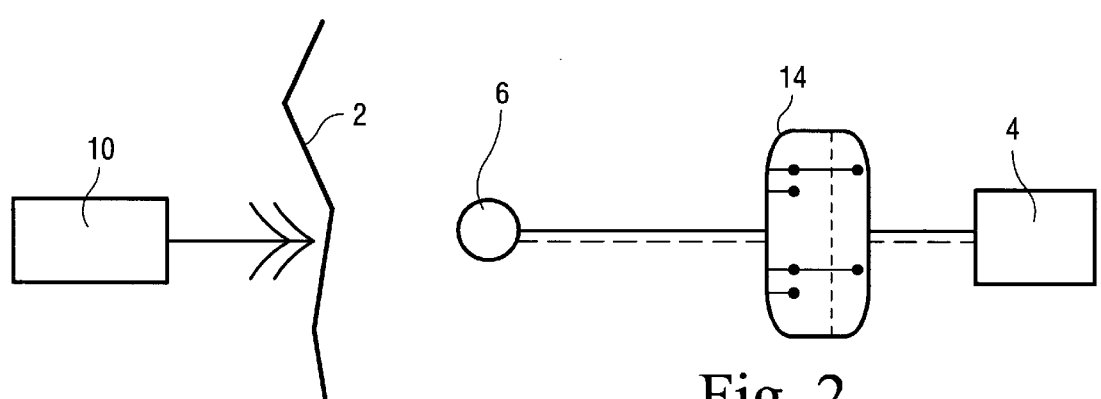

FIG. 2 shows an embodiment of the invention identical to that of FIG. 1, except that a reversing device in the form of a switch 14 operable by polarized energy also is implanted in the patient for reversing the restriction device 4. The control unit 6 uses the switch 14 to reverse the function performed by the restriction device 4. More precisely, the external control unit 10 releases polarized energy carried by a wireless signal and the implanted control unit 6 transfers the wireless polarized energy into a polarized current for operating the switch 14. When the control unit 6 shifts the polarity of the current the switch 14 reverses the function performed by the restriction device 4.

Figure 3:
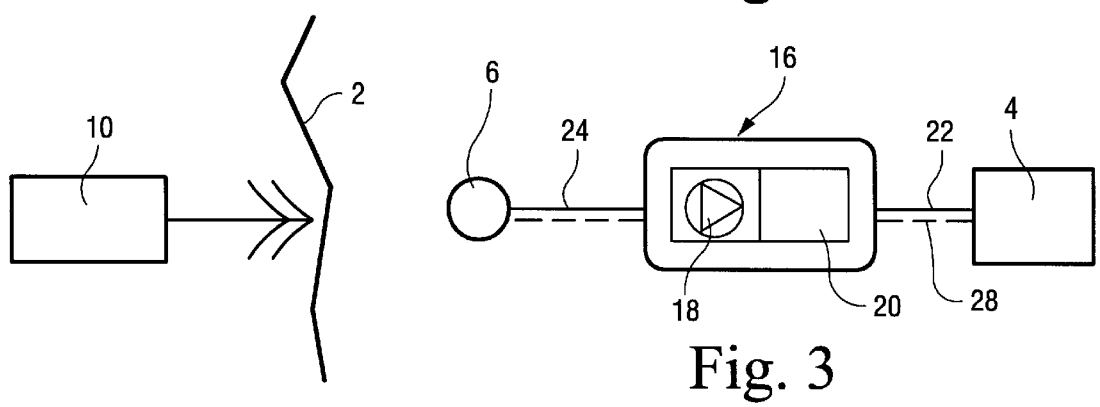

FIG. 3 shows an embodiment of the invention identical to that of FIG. 1, except that an assembly 16 including a motor/pump unit 18 and a fluid reservoir 20 also is implanted in the patient. In this case the restriction device 4 is hydraulically operated, i.e. hydraulic fluid is pumped by the motor/pump unit 18 from the reservoir 20 through a conduit 22 to the restriction device 4 to reduce the cross-sectional area of the food passageway, and hydraulic fluid is pumped by the motor/pump unit 18 back from the restriction device 4 to the reservoir 20 to enlarge the cross-sectional area. The external control unit 10 releases energy carried by a wireless signal and the implanted control unit 6 transfers the wireless energy into a current, for example a polarized current, for powering the motor/pump unit 18 via an electric power supply line 24. The implanted control unit 6 controls the motor/pump unit 16 and the restriction device 4 via control lines 26 and 27.

Figure 4:
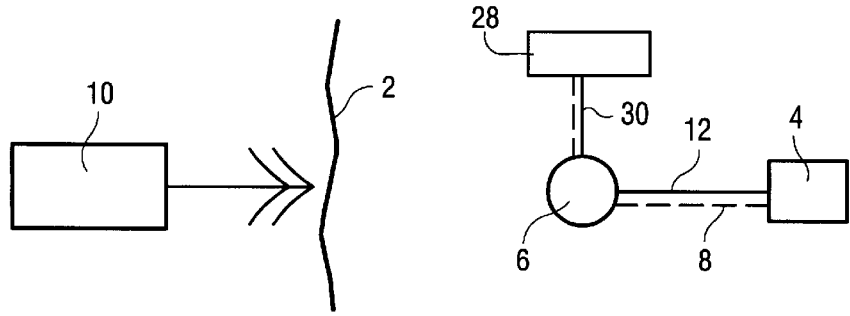

FIG. 4 shows an embodiment of the invention identical to that of FIG. 1, except that an accumulator 28 also is implanted in the patient. The control unit 6 stores energy received from the external control unit 10 in the accumulator 28. In response to a control signal from the external control unit 10 the implanted control unit 6 releases energy from the accumulator 28 via a power line 30 for the operation of the restriction device 4.

Figure 5:
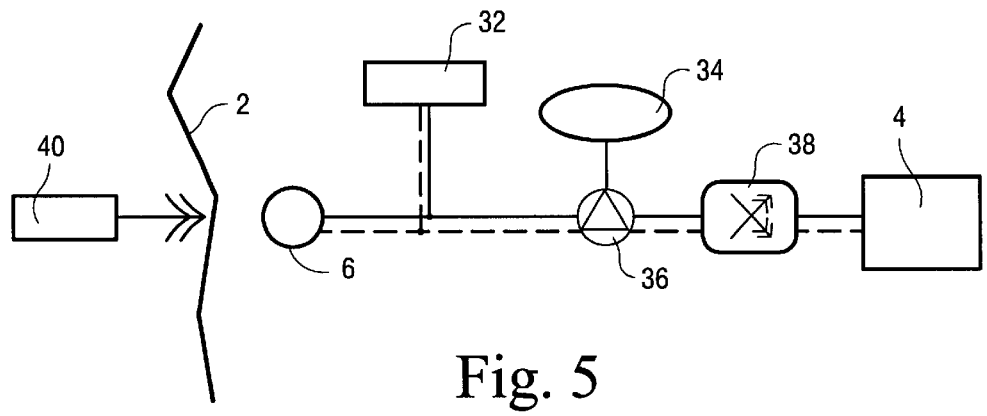
FIGS. 5 to 8 are schematic block diagrams illustrating four embodiments, respectively, of the invention, in which energy is released from an implanted source of energy.

FIG. 5 shows an embodiment of the invention comprising the restriction device 4, hydraulically operated, and the implanted control unit 6, and further comprising a source of energy in the form of a battery 32, a hydraulic fluid reservoir 34, a motor/pump unit 36 and a reversing device in the form of a hydraulic valve shifting device 38, all of which are implanted in the patient. The motor of the motor/pump unit 36 is an electric motor. An external control unit 40 includes a wireless remote control transmitting a control signal which is received by the signal receiver incorporated in the implanted control unit 6.

In response to a control signal from the external control unit 40 the implanted control unit 6 powers the motor/pump unit 36 with energy from the battery 32, whereby the motor/pump unit 36 distributes hydraulic fluid between the reservoir 34 and the restriction device 4. The control unit 6 controls the shifting device 38 to shift the hydraulic fluid flow direction between one direction in which the fluid is pumped by the motor/pump unit 36 from the reservoir 34 to the restriction device 4 to reduce the cross-sectional area of the food passageway, and another opposite direction in which the fluid is pumped by the motor/pump unit 36 back from the restriction device 4 to the reservoir 34 to enlarge the cross-sectional area.

Figure 6:
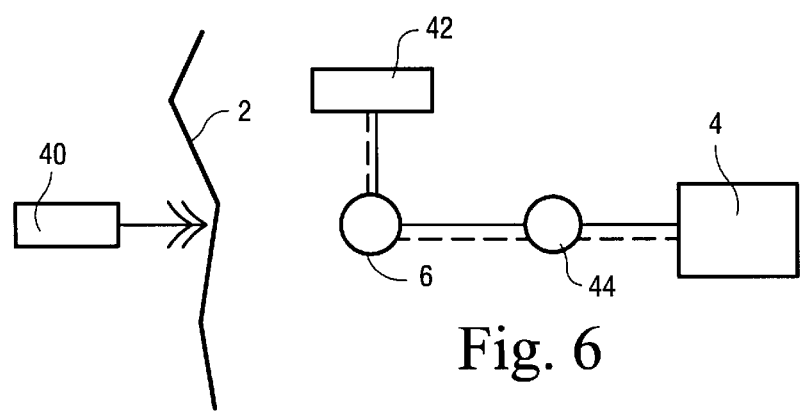

FIG. 6 shows an embodiment of the invention identical to that of FIG. 4, except that a battery 42 is substituted for the accumulator 28, the external control unit 40 of the embodiment of FIG. 5 is substituted for the external control unit 10 and an electric motor 44 is implanted in the patient for operating the restriction device 4. In response to a control signal from the external control unit 40 the implanted control unit 6 powers the motor 44 with energy from the battery 42, whereby the motor 44 operates the restriction device 4.

Figure 7:
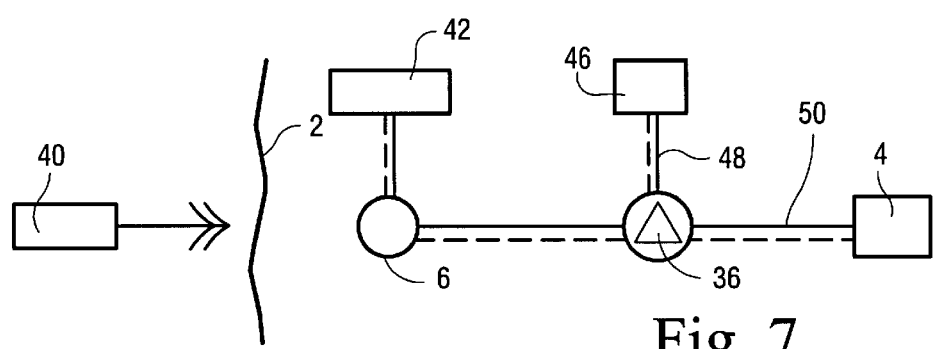

FIG. 7 shows an embodiment of the invention identical to that of FIG. 6, except that the motor/pump unit 36 of the embodiment of FIG. 5 is substituted for the motor 44 and a fluid reservoir 46 also implanted in the patient and via fluid conduits 48 and 50 connected to the motor/pump unit 36 and the restriction device 4, which in this case is hydraulically operated. In response to a control signal from the external control unit 40 the implanted control unit 6 powers the electric motor of the motor/pump unit 36 with energy from the battery 42, whereby the motor/pump unit 36 distributes hydraulic fluid between the fluid reservoir 46 and the restriction device 4.

Figure 8:
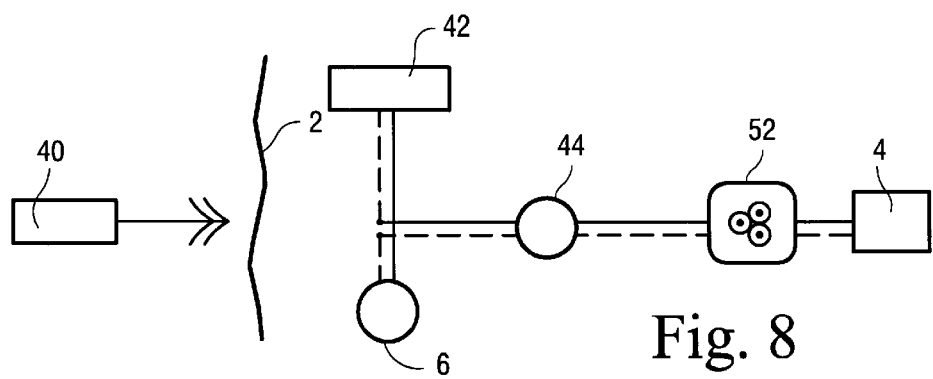

FIG. 8 shows an embodiment of the invention identical to that of FIG. 6, except that a mechanical reversing device in the form of a gear box 52 also is implanted in the patient. The implanted control unit 6 controls the gear box 52 to reverse the function performed by the restriction device 4 (mechanically operated).

Figure 9:
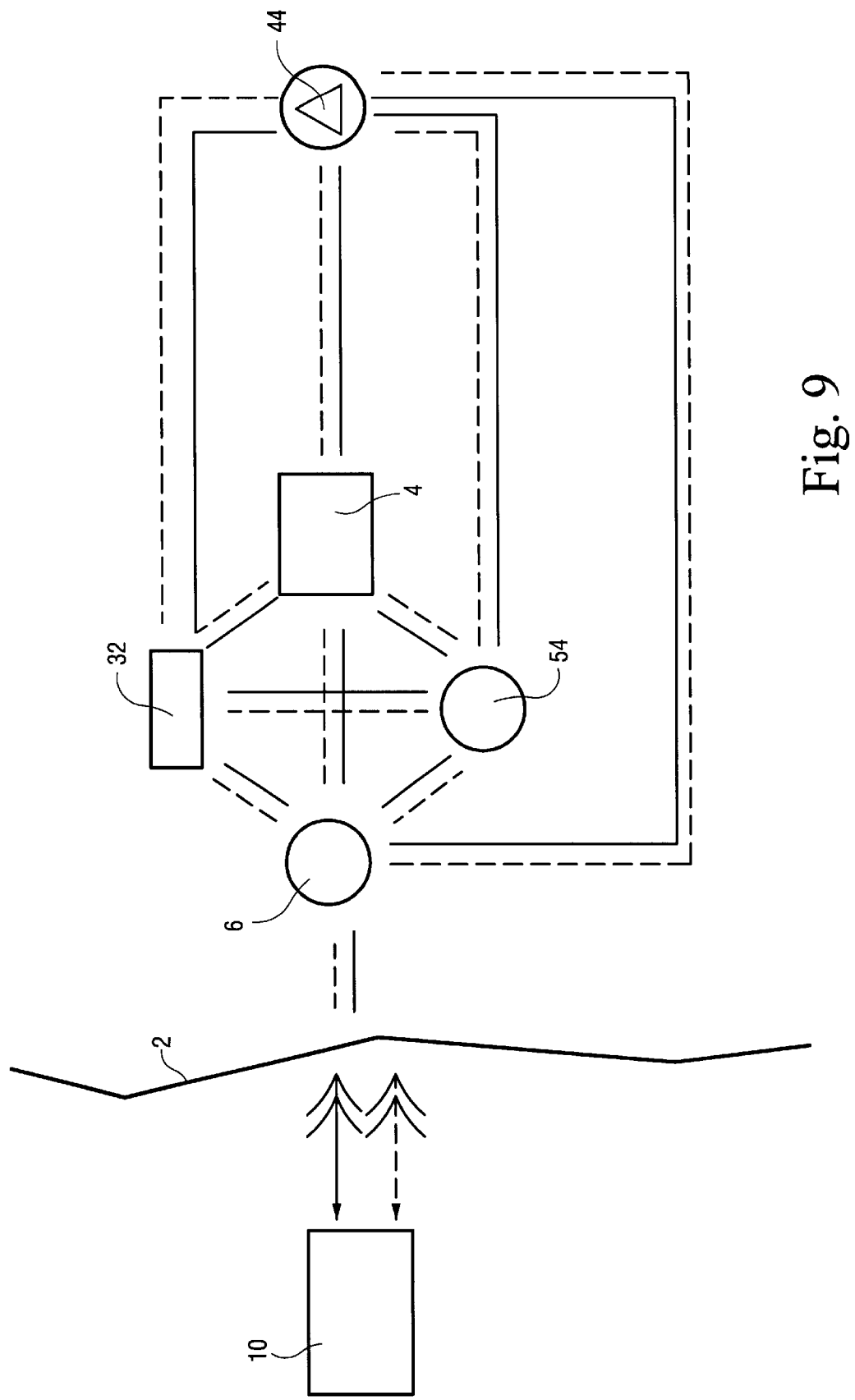
FIG. 9 is a schematic block diagram illustrating conceivable combinations of implanted components for achieving various communication options.

FIG. 9 schematically shows conceivable combinations of implanted components of the apparatus for achieving various communication possibilities. Basically, there are the implanted restriction device 4, the implanted control unit 6 and the external control unit 10 including the external source of energy and the wireless remote control. As already described above the remote control transmits a control signal generated by the external source of energy, and the control signal is received by a signal receiver incorporated in the implanted control unit 6, whereby the control unit 6 controls the implanted restriction device 4 in response to the control signal.

A sensor 54 may be implanted in the patient for sensing a physical parameter of the patient, such as the pressure in the food passageway. The control unit 6, or alternatively the external control unit 10, may control the restriction device 4 in response to sensing from the sensor 54. A tranceiver may be combined with the sensor 54 for sending information on the sensed physical parameter to the external control unit 10. The wireless remote control of the external control unit 10 may comprise a signal transmitter or tranceiver and the implanted control unit 6 may comprise a signal receiver or transciever. Alternatively, the wireless remote control of the external control unit 10 may comprise a signal reciever or transceiver and the implanted control unit 6 may comprise a signal transmitter or transceiver. The above tranceivers, transmitters and receivers may be used for sending information or data related to the restriction device from inside the patient's body to the outside thereof.

The motor 44 may be implanted for operating the restriction device 4 and also the battery 32 may be implanted for powering the motor 44. The battery 32 may be equipped with a tranceiver for sending information on the charge condition of the battery.

Those skilled in the art will realize that the above various embodiments according to FIGS. 1–9 could be combined in many different ways. For example, the polarized energy operated switch 14 could be incorporated in any of the embodiments of FIGS. 3, 4, 6–8, the hydraulic shifting device 38 could be incorporated in any of the embodiments of FIGS. 3 and 7, and the gear box 52 could be incorporated in any of the embodiments of FIGS. 1, 4 and 6.

Figure 10:
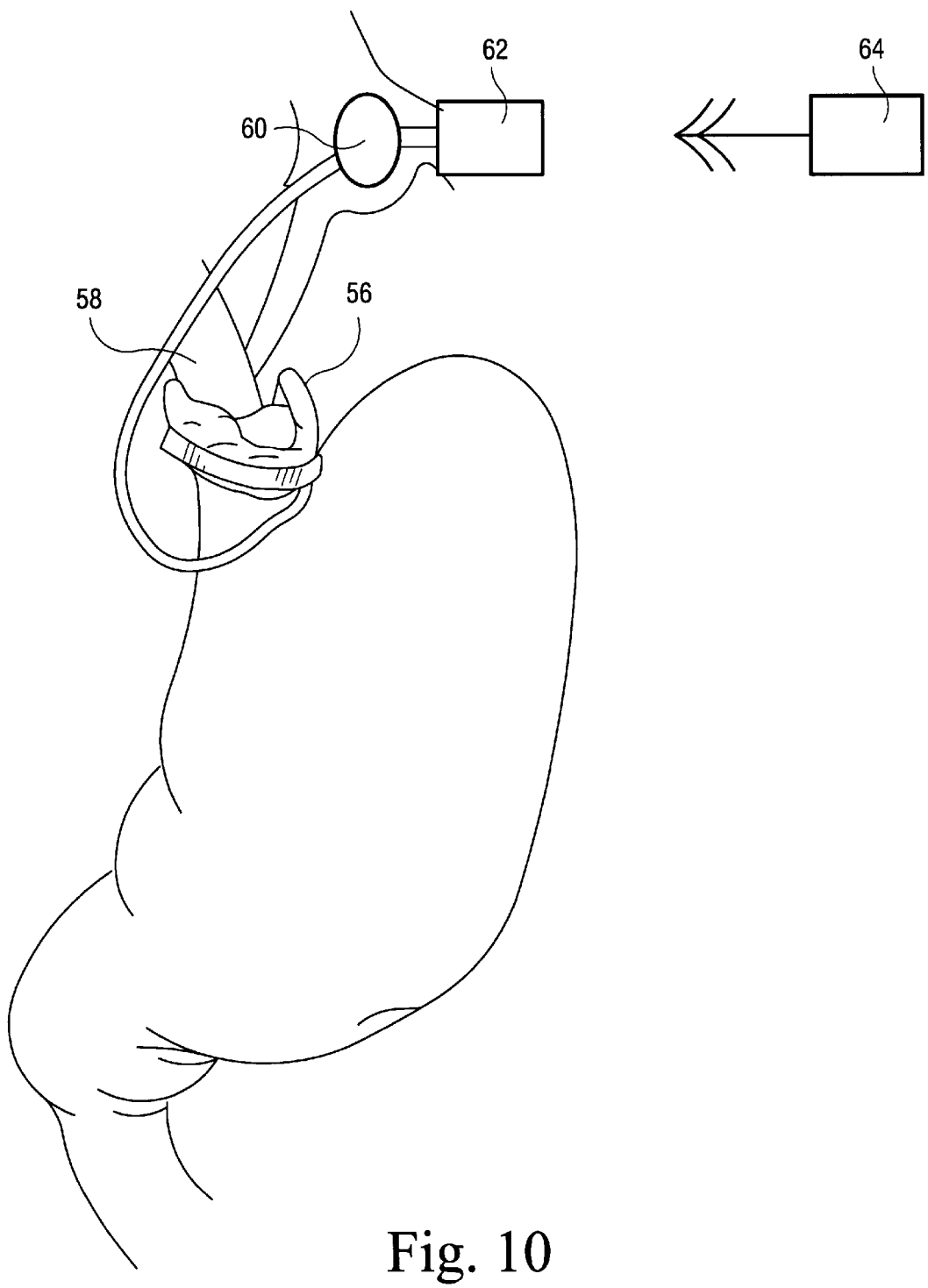
FIG. 10 illustrates the apparatus in accordance with the invention implanted in a patient.

FIG. 10 illustrates how any of the above-described embodiments of the heartburn and reflux disease treatment apparatus of the invention may be implanted in a patient. Thus, an assembly of the apparatus implanted in the patient comprises a restriction device 56 engaging the esophagus 58 close to the cardia, and an operation device 60 for operating the restriction device 56 and an internal control unit 62, which includes a signal receiver, for controlling the operation device 60. An external control unit 64 includes a signal transmitter for transmitting a control signal to the signal receiver of the implanted control unit 62. The implanted control unit 62 is capable of transferring signal energy from the control signal into electric energy for powering the operation device 60 and for energizing energy consuming implanted components of the apparatus.

In the practice of the present invention the details of the elongated restriction device 4, 156 (such as a gastric band) and the adjustment/operation device (which may have electric, hydraulic, or mechanical, etc. actuation) 6, 60 may be as described in copending applications Ser. No. 09/133,319, filed Aug. 13,1998 , U.S. Ser. No. 09/133,320, filed Aug. 13, 1998, and U.S. Ser. No. 09/133,322, filed Aug. 13, 1998, the disclosures of which are incorporated by reference herein.

Figure 11:
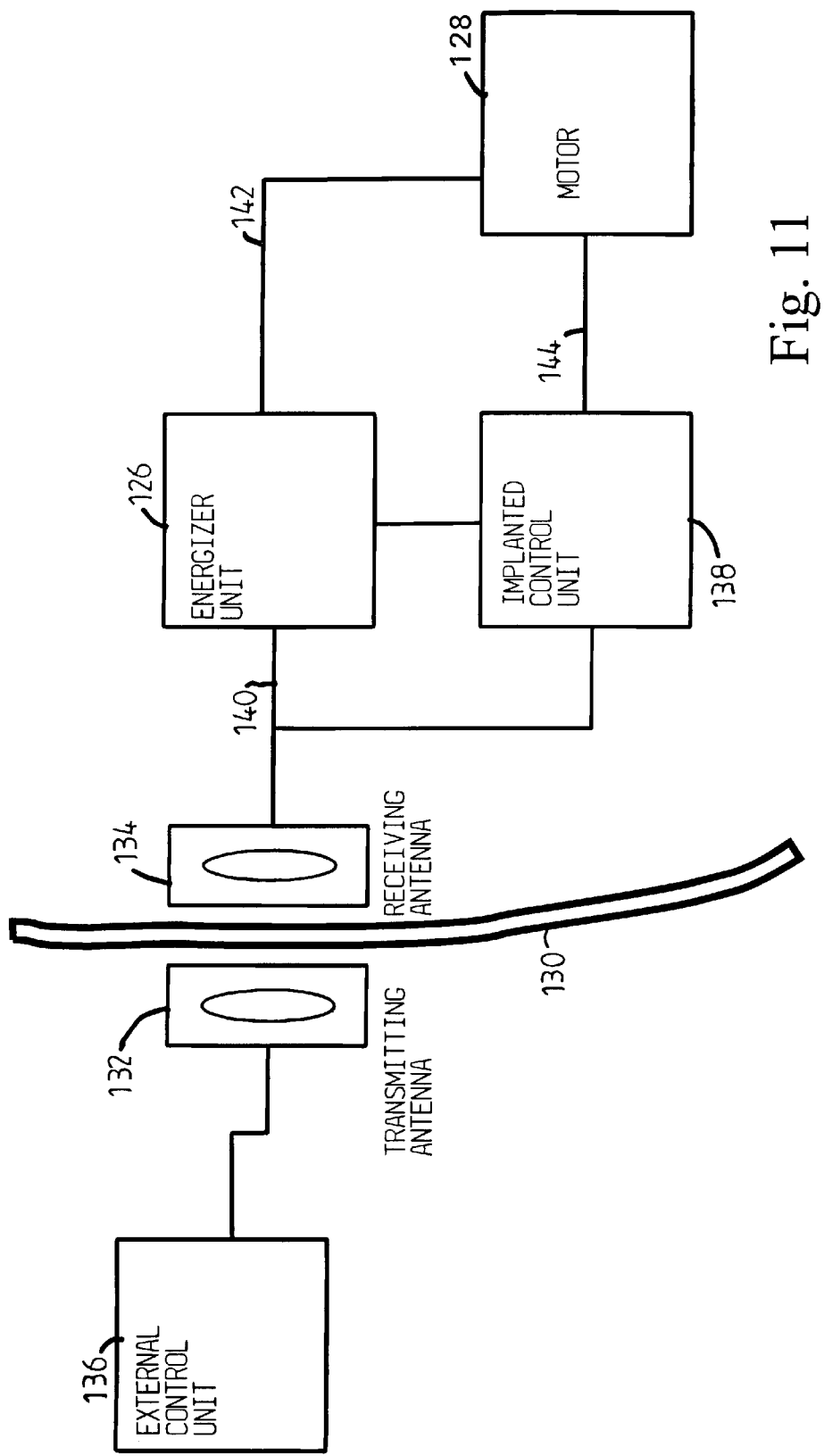
FIG. 11 is a block diagram illustrating remote control components of an embodiment of the invention.

FIG. 11 shows the basic parts of a wireless remote control of the apparatus of the invention including an electric motor 128 for operating a restriction member, for example of the type illustrated in FIG. 10. In this case, the remote control is based on the transmission of electromagnetic wave signals, often of high frequencies in the order of 100 kHz–1 gHz, through the skin 130 of the patient. In FIG. 11, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1–100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either contract or enlarge the restriction device. The microprocessor starts a command by applying a high frequency signal on the antenna 132. After a short time, when the signal has energized the implanted parts of the control system, commands are sent to contract or enlarge the restriction device in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously during a rather long time period (e.g. about 30 seconds or more). When a new contract or enlarge step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signals received by the receiving antenna 134. The energizer unit 126 stores the energy in a power supply, such as a large capacitor, powers the control unit 138 and powers the electric motor 128 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 128 to either contract or enlarge the restriction device depending on the received command code.

Alternatively, the energy stored in the power supply of the energizer unit may only be used for powering a switch, and the energy for powering the motor 128 may be obtained from another implanted power source of relatively high capacity, for example a battery. In this case the switch is adapted to connect said battery to the control unit 138 in an "on" mode when said switch is powered by said power supply and to keep said battery disconnected from the control unit in a "standby" mode when said switch is unpowered.

Figure 12:
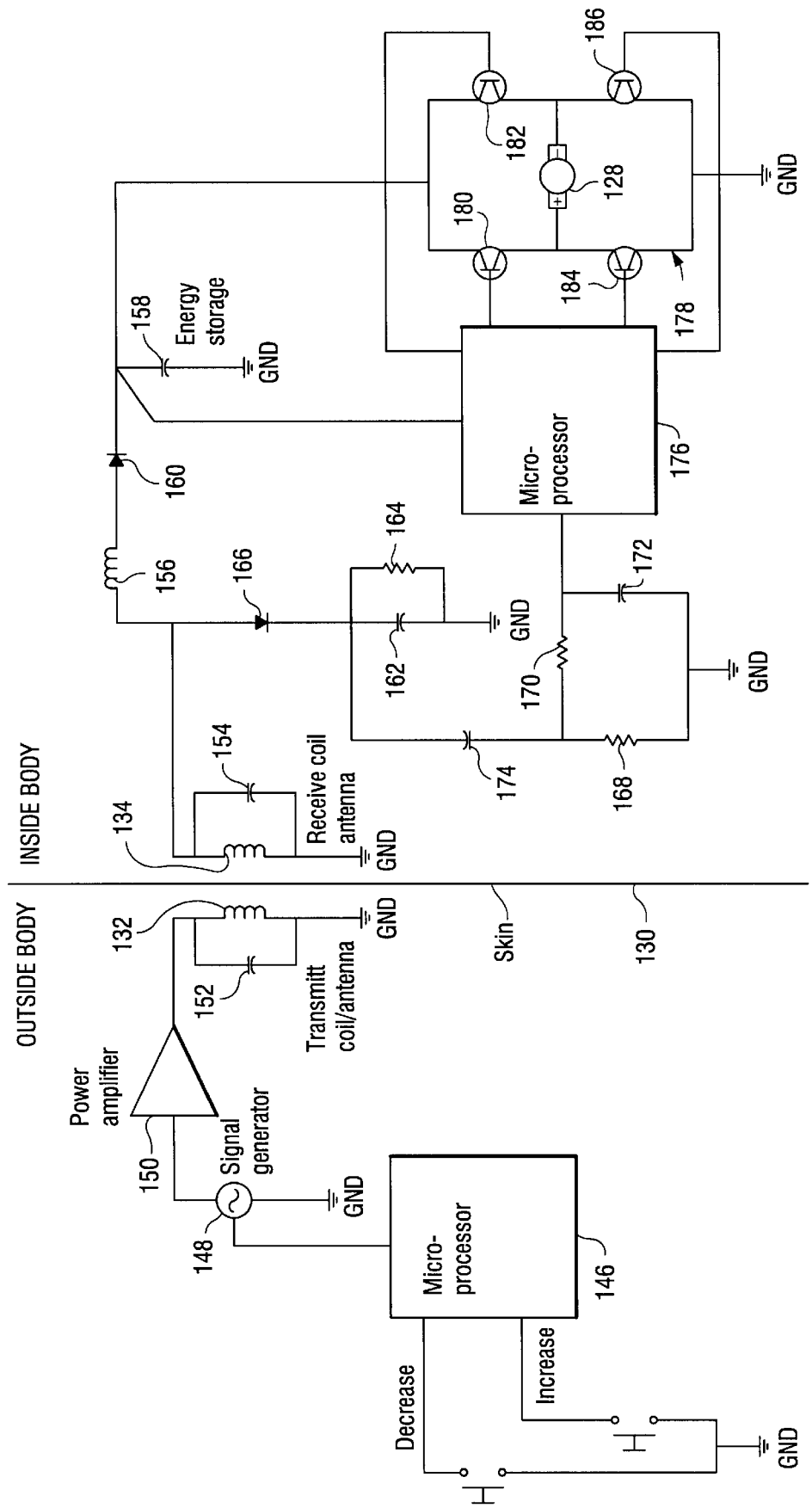
FIG. 12 is a schematic view of exemplary circuitry used for the components of the block diagram of FIG. 11.

With reference to FIG. 12, the remote control schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168, 170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 128 via an H-bridge 178 comprising transistors 180,182,184 and 186. The motor 128 can be driven in two opposite directions by the H-bridge 178.

The microprocessor 176 also monitors the amount of stored energy in the storage capacitor 158. Before sending signals to activate the motor 128, the microprocessor 176 checks whether the energy stored in the storage capacitor 158 is enough. If the stored energy is not enough to perform the requested operation, the microprocessor 176 waits for the received signals to charge the storage capacitor 158 before activating the motor 128.

What is claimed is:

1. A heartburn and reflux disease treatment apparatus, comprising: an operable restriction device adapted to be implanted in a patient having heartburn and reflux disease to engage the esophagus or the stomach close to the cardia without forming an upper pouch of the stomach that substantially accumulates food to form a restricted food passageway in the stomach or esophagus, said restriction device being designed to work like an artificial sphincter to allow food to readily pass through the passageway, a source of energy, and a control device operable from outside the patient's body for releasing energy from said source of energy for use in operating said restriction device to restrict the passageway sufficiently so as to substantially prevent regurgitation of stomach acids or foods into the patient's esophagus.

2. The apparatus according to claim 1, wherein said control device controls said restriction device.

3. The apparatus according to claim 2, wherein said control device comprises an internal control unit adapted to be implanted in the patient for controlling said operation device.

4. The apparatus according to claim 3, wherein said internal control unit is programmable.

5. The apparatus according to claim 4, wherein said control device comprises an external control unit outside the patient's body, said internal control unit being programmable by said external control unit.

6. The apparatus according to claim 5, wherein said external control unit loads said internal control unit with data in accordance with a loading mode only authorized for a doctor.

7. The apparatus according to claim 5, wherein said external control unit controls said internal control unit in accordance with a doctor mode only authorized for a doctor.

8. The apparatus according to claim 5, wherein said external control unit controls said internal control unit in accordance with a patient mode permitted for the patient.

9. The apparatus according to claim 4, wherein said internal control unit is programmable for controlling said restriction device over time.

10. The apparatus according to claim 9, wherein said internal control unit controls said restriction device over time in accordance with an activity schedule program.

11. The apparatus according to claim 9, wherein said internal control unit comprises a microprocessor.

12. The apparatus according to claim 1, further comprising an operation device adapted to be implanted in the patient for operating said restriction device, wherein said control device controls said operation device to operate said restriction device.

13. The apparatus according to claim 12, wherein said operation device comprises hydraulic means and at least one valve for controlling a fluid flow in said hydraulic means.

14. The apparatus according to claim 13, wherein said control device comprises a wireless remote control for controlling said valve.

15. The apparatus according to claim 12, wherein said restriction device comprises hydraulic means and said operation device comprises a reservoir forming a fluid chamber with a variable volume connected to said hydraulic means, and said operation device distributes fluid from said chamber to said hydraulic means by reduction of the volume of said chamber and withdraws fluid from said hydraulic means to said chamber by expansion of the volume of said chamber.

16. The apparatus according to claim 12, wherein said source of energy is adapted to be external to the patient's body and said control device releases wireless energy from said external source of energy.

17. The apparatus according to claim 16, wherein said operation device comprises a motor.

18. The apparatus according to claim 17, wherein said motor comprises a rotary motor, and said control device controls said rotary motor to rotate a desired number of revolutions.

19. The apparatus according to claim 17, wherein said motor comprises a linear motor.

20. The apparatus according to claim 17, wherein said motor comprises a hydraulic or pneumatic fluid motor, and said control device controls said fluid motor.

21. The apparatus according to claim 17, wherein said motor comprises an electric motor having electrically conductive parts made of plastics.

22. The apparatus according to claim 16, wherein said control device releases polarized energy from said external source of energy.

23. The apparatus according to claim 16, wherein said control device shifts polarity of said released energy to reverse said operation device.

24. The apparatus according to claim 16, wherein said operation device comprises an electric motor and said released energy comprises electric energy.

25. The apparatus according to claim 16, wherein said restriction device is operable to perform a reversible function.

26. The apparatus according to claim 25, further comprising a reversing device adapted to be implanted in the patient for reversing said function performed by said restriction device.

27. The apparatus according to claim 26, wherein said control device controls said reversing device to reverse said function performed by said restriction device.

28. The apparatus according to claim 27, wherein said reversing device comprises a switch.

29. The apparatus according to claim 28, wherein said switch is operable by said released energy.

30. The apparatus according to claim 29, wherein said control device controls the operation of said switch by shifting polarity of said released energy supplied to said switch.

31. The apparatus according to claim 26, wherein said reversing device comprises a mechanical reversing device.

32. The apparatus according to claim 31, wherein said mechanical reversing device comprises a switch.

33. The apparatus according to claim 31, wherein said reversing device comprises a gear box.

34. The apparatus according to claim 26, wherein said reversing device comprises hydraulic means including a valve for shifting the flow direction of a fluid in said hydraulic means.

35. The apparatus according to claim 28, wherein said switch comprises an electric switch and said source of energy supplies electric energy for the operation of said switch.

36. The apparatus according to claim 28, wherein said operation device comprises a motor, and said reversing device reverses said motor.

37. The apparatus according to claim 16, further comprising a battery adapted to be implanted in the patient for supplying electric energy to implantable electric energy consuming components of the apparatus.

38. The apparatus according to claim 16, further comprising an energy storage device adapted to be implanted in the patient for storing said wireless energy released from said external source of energy.

39. The apparatus according to claim 38, wherein said energy storage device comprises an accumulator.

40. The apparatus according to claim 39, wherein said accumulator comprises an electric accumulator.

41. The apparatus according to claim 40, wherein said electric accumulator comprises at least one capacitor or at least one rechargeable battery, or a combination of at least one capacitor and at least one rechargeable battery.

42. The apparatus according to claim 16, wherein said restriction device comprises hydraulic means and said operation device comprises a pump for pumping a fluid in said hydraulic means.

43. The apparatus according to claim 42, wherein said operation device comprises a motor for driving said pump.

44. The apparatus according to claim 43, wherein said operation device comprises a fluid conduit between said pump and said hydraulic means of said restriction device, and a reservoir for fluid, said reservoir forming part of said conduit.

45. The apparatus according to claim 44, wherein said hydraulic means, pump and conduit is devoid of any non-return valve.

46. The apparatus according to claim 45, wherein said reservoir forms a fluid chamber with a variable volume, and said pump distributes fluid from said chamber to said hydraulic means of said restriction device by reduction of the volume of said chamber and withdraws fluid from said hydraulic means to said chamber by expansion of the volume of said chamber.

47. The apparatus according to claim 1, wherein said source of energy is adapted to be implanted in the patient.

48. The apparatus according to claim 47, wherein said implantable source of energy comprises at least one accumulator, at least one capacitor or at least one rechargeable battery, or a combination of at least one capacitor and at least one rechargeable battery.

49. The apparatus according to claim 48, wherein said implantable source of energy comprises an electric source of energy.

50. The apparatus according to claim 49, wherein said electric source of energy comprises an accumulator, or a battery having a life-time of at least 10 years.

51. The apparatus according to claim 47, wherein said control device controls said restriction device.

52. The apparatus according to claim 51, further comprising an operation device adapted to be implanted in the patient for operating said restriction device, wherein said control device controls said operation device to operate said restriction device.

53. The apparatus according to claim 52, wherein said operation device comprises a motor.

54. The apparatus according to claim 53, wherein said motor comprises a rotary motor, and said control device controls said rotary motor to rotate a desired number of revolutions.

55. The apparatus according to claim 53, wherein said motor comprises a hydraulic or pneumatic fluid motor, and said control device controls said fluid motor.

56. The apparatus according to claim 53, wherein said motor comprises a casing of electrically conductive plastics.

57. The apparatus according to claim 51, wherein said control device releases energy from said implantable source of energy.

58. The apparatus according to claim 51, wherein said control device shifts polarity of said released energy to reverse said operation device.

59. The apparatus according to claim 58, wherein said restriction device comprises hydraulic means, and said operation device comprises a pump for pumping a fluid in said hydraulic means and a motor for driving said pump.

60. The apparatus according to claim 51, wherein said operation device comprises an electric motor and said released energy comprises electric energy.

61. The apparatus according to claim 47, wherein said restriction device is operable to perform a reversible function.

62. The apparatus according to claim 61, further comprising a reversing device adapted to be implanted in the patient for reversing said function performed by said restriction device.

63. The apparatus according to claim 62, wherein said control device controls said reversing device to reverse said function performed by said restriction device.

64. The apparatus according to claim 62, wherein said reversing device comprises hydraulic means including a valve for shifting the flow direction of a fluid in said hydraulic means.

65. The apparatus according to claim 62, wherein said reversing device comprises a mechanical reversing device.

66. The apparatus according to claim 65, wherein said mechanical reversing device comprises a switch.

67. The apparatus according to claim 65, wherein said mechanical reversing device comprises a gear box.

68. The apparatus according to claim 62, wherein said reversing device comprises a switch.

69. The apparatus according to claim 68, wherein said switch is operable by energy released from said source of energy.

70. The apparatus according to claim 68, wherein said control device controls the operation of said switch by shifting polarity of said released energy supplied to said switch.

71. The apparatus according to claim 68, wherein said switch comprises an electric switch and said source of energy supplies electric energy for the operation of said switch.

72. The apparatus according to claim 62, wherein said operation device comprises a motor, and said reversing device reverses said motor.

73. The apparatus according to claim 52, wherein said restriction device comprises hydraulic means, and said operation device comprises a pump for pumping a fluid in said hydraulic means and a motor for driving said pump.

74. The apparatus according to claim 73, wherein said operation device comprises a fluid conduit between said pump and said hydraulic means of said restriction device, and a reservoir for fluid, said reservoir forming part of said conduit.

75. The apparatus according to claim 74, wherein said hydraulic means, pump and conduit are devoid of any non-return valve.

76. The apparatus according to claim 74, wherein said reservoir forms a fluid chamber with a variable volume, and said pump distributes fluid from said chamber to said hydraulic means of said restriction device by reducing the volume of said chamber and withdraws fluid from said hydraulic means to said chamber by expanding the volume of said chamber.

77. The apparatus according to claim 1, further comprising at least one sensor adapted to be implanted in the patient for sensing at least one physical parameter of the patient.

78. The apparatus according to claim 77, wherein said control device controls said restriction device in response to signals from said sensor.

79. The apparatus according to claim 78, wherein said control device comprises an internal control unit adapted to be implanted in the patient, said internal control unit directly controlling said restriction device in response to signals from said sensor.

80. The apparatus according to claim 78, wherein said control device comprises an external control unit outside the patient's body, said external control unit controlling said restriction device in response to signals from said sensor.

81. The apparatus according to claim 80, wherein said external control unit directly controls said restriction device in response to signals from said sensor.

82. The apparatus according to claim 80, wherein said external control unit stores information on said physical parameter sensed by said sensor and is manually operated to control said restriction device based on said stored information.

83. The apparatus according to claim 77, further comprising at least one sender adapted to be implanted in the patient for sending information on said physical parameter sensed by said sensor.

84. The apparatus according to claim 1, further comprising an external data communicator outside the patient's body and an internal data communicator adapted to be implanted in the patient for communicating with said external data communicator, wherein said internal data communicator feeds data related to the patient back to said external data communicator or said external data communicator feeds data to said internal data communicator.

85. The apparatus according to claim 84, wherein said internal data communicator feeds data related to said restriction device.

86. The apparatus according to claim 84, wherein said internal data communicator feeds data related to at least one physical signal of the patient.

87. The apparatus according to claim 1, further comprising a switch adapted to be implanted in the patient for directly or indirectly switching said energy released from said source of energy.

88. The apparatus according to claim 1, wherein said restriction device is adapted to control the cross-sectional area of the food passageway.

89. The apparatus according to claim 88, wherein said restriction device is operable to open and close the food passageway.

90. The apparatus according to claim 88, wherein said restriction device is adapted to steplessly control the cross-sectional area of the food passageway.

91. The apparatus according to claim 1, further comprising
a pressure sensor for directly or indirectly sensing the pressure in the food passageway.

92. The apparatus according to claim 91, wherein said control device controls said restriction device in response to sensing from said pressure sensor.

93. The apparatus according to claim 1, further comprising an energy transfer device adapted to be implanted in the patient, wherein said control device releases electric energy and said energy transfer device transfers said electric energy into kinetic energy for operation of said restriction device.

94. The apparatus according to claim 93, further comprising a capacitor adapted to be implanted in the patient for stabilizing said electric energy released by said control device.

95. The apparatus according to claim 93, wherein said restriction device is directly operated with said kinetic energy, as said energy transfer device transfers said electric energy into kinetic energy.

96. The apparatus according to claim 1, wherein said restriction device is non-inflatable.

97. The apparatus according to claim 1, wherein said control device releases energy for a determined time period.

98. The apparatus according to claim 1, wherein said control device releases energy in a determined number of energy pulses.

99. The apparatus according to claim 1, wherein said control device comprises a wireless remote control transmitting at least one wireless control signal for controlling said restriction device.

100. The apparatus according to claim 99, wherein said remote control is capable of obtaining information on the condition of said restriction device and of controlling said restriction device in response to said information.

101. The apparatus according to claim 99, wherein said wireless remote control comprises at least one external signal transmitter or transceiver and at least one internal signal receiver or transceiver adapted to be implanted in the patient.

102. The apparatus according to claim 99, wherein said wireless remote control comprises at least one external signal receiver or transceiver and at least one internal signal transmitter or transceiver adapted to be implanted in the patient.

103. The apparatus according to claim 99, wherein said remote control is capable of sending information related to said restriction device from inside the patient's body to the outside thereof.

104. The apparatus according to claim 103, wherein said remote control controls said restriction device in response to said information.

105. The apparatus according to claim 99, wherein said remote control transmits a carrier signal for carrying said control signal.

106. The apparatus according to claim 105, wherein said carrier signal is frequency, amplitude or frequency and amplitude modulated.

107. The apparatus according to claim 105, wherein said carrier signal is digital, analog or digital and analog.

108. The apparatus according to claim 105, wherein said control signal used with said carrier signal is frequency, amplitude or frequency and amplitude modulated.

109. The apparatus according to claim 99, wherein said control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

110. The apparatus according to claim 99, wherein said control signal comprises an electric, magnetic or electric and magnetic field.

111. The apparatus according to claim 99, wherein said control signal is digital, analog or digital and analog.

112. The apparatus according to claim 111, wherein said remote control transmits an electromagnetic carrier wave signal for carrying said digital or analog control signal.

113. The apparatus according to claim 99, wherein said control signal is transmitted in pulses by said wireless remote control.

114. The apparatus according to claim 1, wherein said control device releases energy from said source of energy in a non-invasive manner.

115. apparatus according to claim 1, wherein said control device releases magnetic energy.

116. The apparatus according to claim 1, wherein said control device releases electromagnetic energy.

117. The apparatus according to claim 1, wherein said control device releases kinetic energy.

118. The apparatus according to claim 1, wherein said control device releases thermal energy.

119. The apparatus according to claim 1, wherein said control device releases energy from said source of energy in a mechanical manner.

120. The apparatus according to claim 1, wherein said control device releases non-magnetic energy.

121. The apparatus according to claim 1, wherein said control device releases non-electromagnetic energy.

122. The apparatus according to claim 1, wherein said control device releases non-kinetic energy.

123. The apparatus according to claim 1, wherein said control device releases non-thermal energy.

124. The apparatus according to claim 1, wherein said control device releases energy from said source of energy in a non-mechanical manner.

125. A method of treating a patient having heartburn and reflux disease, comprising:

(a) implanting in the patient an operable restriction device, so that the restriction device engages the stomach close to the cardia or engages the esophagus without forming an upper pouch of the stomach that substantially accumulates food to form a restricted food passageway in the stomach or esophagus, (b) implanting in the patient a source of energy, (c) implanting in the patient an operation device for operating said restriction device, (d) controlling the source of energy to release energy, and (e) using the released energy to activate the implanted operation device so as (i) to enlarge the restricted food passageway to allow food to readily pass therethrough into the patient's stomach, or to allow the patient to regurgitate, or (ii) to restrict the restricted food passageway sufficiently so as to substantially prevent regurgitation of stomach acids and foods into the esophagus.

126. A method of treating a patient having heartburn and reflux disease, comprising the steps of:

(a) placing at least two laparoscopical trocars in the patient's body, (b) inserting a dissecting tool through the trocars and dissecting an area of the stomach or esophagus, (c) placing an operable restriction device in the dissected area, so that the restriction device engages the stomach close to the cardia or engages the esophagus without forming an upper pouch of the stomach that substantially accumulates food to form a restricted food passageway in the stomach or esophagus, (d) implanting a source of energy in the patient, (e) implanting in the patient an operation device for operating said restriction device, (f) controlling the source of energy from outside the patient's body to release energy, and (g) using the released energy to activate the implanted operation device so as to (i) enlarge the restricted food passageway to allow food to readily pass therethrough into the patient's stomach, or to allow the patient to regurgitate, or (ii) restrict the restricted food passageway sufficiently so as to substantially prevent regurgitation of stomach acids and foods into the esophagus.

127. A method of treating heartburn and reflux disease, comprising the steps of:

placing at least two laparascopical trocars in a patient's body, inserting a dissecting tool through the trocars and dissecting an area of the stomach or esophagus, implanting an operable restriction device in the dissected area, so that the restriction device engages the stomach close to the cardia or engages the esophagus without forming an upper pouch of the stomach that substantially accumulates food to form a restricted food passageway in the stomach or esophagus, implanting an internal source of energy in the patient, providing an external source of energy, controlling the external source of energy to release wireless energy, transferring the wireless energy released from the external energy into storable energy, charging the internal source of energy with the storable energy, and using energy from the internal source of energy for operating the restriction device to restrict the passageway sufficiently so as to substantially prevent regurgitation of stomach acids or foods into the patient's esophagus.

* * * * *